United States Patent
Hoogland

(10) Patent No.: US 6,682,535 B2
(45) Date of Patent: Jan. 27, 2004

(54) APPARATUS FOR DECOMPRESSING HERNIATED INTERVERTEBRAL DISCS

(76) Inventor: Thomas Hoogland, c/o Alpha-Klinik, Effnerstrasse 38, D-81925 Munich (DE)

(*) Notice: Subject to any disclaimer, the term of this patent is extended or adjusted under 35 U.S.C. 154(b) by 75 days.

(21) Appl. No.: 10/015,685

(22) Filed: Dec. 17, 2001

(65) Prior Publication Data

US 2002/0091387 A1 Jul. 11, 2002

Related U.S. Application Data

(63) Continuation of application No. PCT/EP00/04177, filed on Jun. 16, 1999.

(51) Int. Cl.[7] .................. A61B 17/16; A61B 17/56; A61B 17/28
(52) U.S. Cl. .................. 606/80; 606/96; 606/179; 606/190; 606/205
(58) Field of Search .................. 606/61, 79, 80, 606/82, 96, 108, 167, 170, 176, 179, 180, 184, 185, 190

(56) References Cited

U.S. PATENT DOCUMENTS

| | | | |
|---|---|---|---|
| 4,573,448 A | 3/1986 | Kambin | |
| 4,696,308 A | * | 9/1987 | Meller et al. |
| 5,241,972 A | * | 9/1993 | Bonati |

FOREIGN PATENT DOCUMENTS

| | | |
|---|---|---|
| EP | 0 890 341 A | 1/1999 |
| FR | 2 714 285 A | 6/1995 |
| WO | WO 93 04652 A | 3/1993 |

\* cited by examiner

Primary Examiner—David O. Reip
(74) Attorney, Agent, or Firm—Sughrue Mion, PLLC

(57) ABSTRACT

The invention provides a method of and an apparatus for removing bone, capsule ligaments from a co-operating pair of superior and inferior articulating processes (also called facet joints) of the spine to create a path for postero-lateral endoscopic access to the vertebral foramen and to the epidural space of the spinal canal; successively advancing tools (64) of an increasing diameter along the path; advancing through a working cannula (40) of an endoscope in order to visualize the herniated disc material and to check for the presence of nerve roots or dural sac; and engaging soft tissue with a tool in the working cannula, the soft tissue deriving from the herniated disc, and withdrawing the tissue through the cannula, hereby to relieve pressure on nerve structures within the vertebral foramen and spinal canal.

5 Claims, 2 Drawing Sheets

APPARATUS FOR DECOMPRESSING HERNIATED INTERVERTEBRAL DISCS

This is a continuation of Application No. PCT/EP00/04177 filed Jun. 16, 1999; the above noted prior applications are all hereby incorporated by reference; the international application to which benefit is claimed was published under PCT Article 21(2) in English.

FIELD OF INVENTION

This invention relates to a method of and apparatus to remove a protruded, extruded or herniated disc or to decompress a spinal nerve route from lateralstenosis.

PRIOR ART

U.S. Pat. No. 4,573,448 discloses a method of decompressing herniated discs in the lumbar spine, which can be carried out percutaneously by the insertion of a trocar and cannula over a guidewire extending through the patient's back towards the herniated disc at an angle of approximately 35 degrees with respect to the patient's perpendicular line. A hollow cutting instrument is inserted through the cannula to form a window in the disc. Disc fragments are removed through the cannula by means of a forceps instrument. It is disclosed that, as the disc is decompressed, the herniation recedes. It is also stated that, in some cases, it is possible to position the instruments so that the cutting instrument enters the bulge of herniation. As the patent explains, it is a virtue of its postero-lateral endoscopic access that the need for bone removal is avoided, and with it the likely resulting complications.

The patent explains that patients treated in accordance with this new procedure are generally able to ambulate and to sit on the day of surgery, or one day afterwards, that post-operative back pain was minimal and that hospitalisation time is typically as little as two days.

However, the patent also explains that there is a risk of re-herniation through the entry window of the cutting instrument into the disc. As is pointed out in the patent, however, the location of this fenestration, produced by the operation, is such that any re-herniation which does occur is much less likely to apply pressure to the patient's nerve roots than the original herniation treated by the operative procedure.

It is one aim of the present invention to achieve the benefits of the postero-lateral endoscopic access described in the above US patent, yet at the same time mitigating the disadvantages arising from an operatively produced annulus fenestration in the herniated disc.

SUMMARY OF THE INVENTION

According to one aspect of the present invention there is provided a method of treating a herniated spinal disc or to decompress a spinal nerve root encroached by stenosis, including the steps of:
1. removing bone, capsule and capsular ligaments from a co-operating pair of superior and inferior articulating processes (also called facet joints) of the spine to create a path for postero-lateral endoscopic access to the vertebral foramen and to the epidural space of the spinal canal;
2. successively advancing tools of an increasing diameter along said path;
3. advancing through a working cannula of an endoscope in order to visualise the herniated disc material and to check for the presence of nerve roots or dural sac; and
4. engaging soft tissue with a tool in the working cannula, said soft tissue deriving from said herniated disc, and withdrawing said tissue through the cannula, hereby to relieve pressure on nerve structures within the vertebral foramen and spinal canal.

It will be appreciated that, with the method of the present invention, there is no operative invasion of the intact annulus fibrosis of the disc. It is the removal of bone from the articulating process, or facet joint, of the spine, adjacent to the herniated disc, which allows removal of the herniation without penetration into the intact annulus of the disc itself. This bone removal is tolerable because adverse consequences for the patient are significantly less than with the prior art disc-penetrative methods.

In this context, it should be observed that surgical removal of a disc herniation, from within the vertebral canal, using a fully posterior approach, has previously been proposed. However, it is a disadvantage with such a procedure that the nerve structures within the foramen have to be displaced to one side in order to give access to the herniation, and this lateral displacement can be damaging and often creates scar tissue. The presence of this scar tissue usually has adverse consequences and, for this reason, a fully posterior approach is not the method of choice.

In another aspect of the present invention, there is provided apparatus for treating a herniated disc, the apparatus comprising an endoscopic soft tissue removal tool and a working cannula through which said tool can be advanced, the apparatus being characterised by:
  means for removing bone from a co-operating pair of superior and inferior articulating processes of the spine, to create a path for postero-lateral endoscopic access to the vertebral foramen and vertebral canal.

In one preferred embodiment, the bone removal means comprises a set of trocar rods of progressively increasing outside diameter, and a corresponding set of hole saw tools, each of which fits snugly over the outside diameter of its corresponding trocar tube and is rotatable on the tube in order to bore through the bony material around the facet joint of the spine corresponding to the herniated spinal disc under treatment.

In one preferred embodiment, the set of hole saw tools has a smallest member with an outside diameter of 5.5 mm and a largest member with an outside diameter of 8.5 mm, with the intervening sizes of hole saws having outside diameters of 6.5 and 7.5 mm, there being four saws in the set. Each of the tools is made of material with a wall thickness of 0.7 mm, so that the corresponding inside diameters of the four saw tools also differ by a 1.0 mm step, from 4.1 mm for the smallest diameter, to 7.1 mm for the largest diameter tool. The four corresponding trocar tools have outside diameters of 4, 5, 6 and 7 mm respectively. The final working cannulas have an outside diameter of respectively 6.5, 7.5 and 8.5 mm.

BRIEF DESCRIPTION OF THE DRAWINGS

For a better understanding of the present invention, and to show more clearly how the same may be carried into effect, reference will now be made, by way of example, to the accompanying drawings, in which.

DETAILED DESCRIPTION OF THE INVENTION

Figure 1:
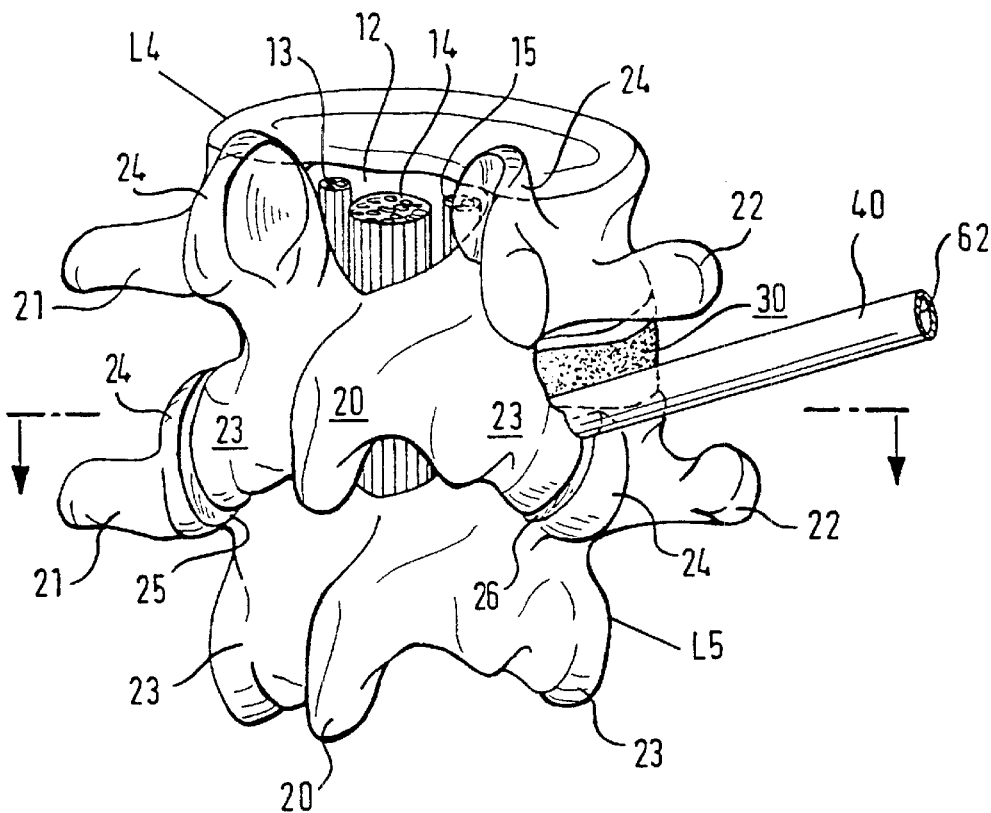
FIG. 1 is a posterior view of two adjacent lumbar vertebrae of a human spine.

Looking first at FIG. 1, the example given is of the disc between the fourth and fifth vertebra L4 and the fifth and lowest lumbar vertebra L5. Within the vertebral canal 12, nerve structures 13, 14 and 15 are diagramatically represented. Each vertebra has a spinous process 20, left transverse process 21, right transverse process 22, left and right inferior articular processes 23 and left and right superior articular processes 24. These articular processes create, level with each disc, a left facet joint 25 and a right facet joint 26.

Figure 2:
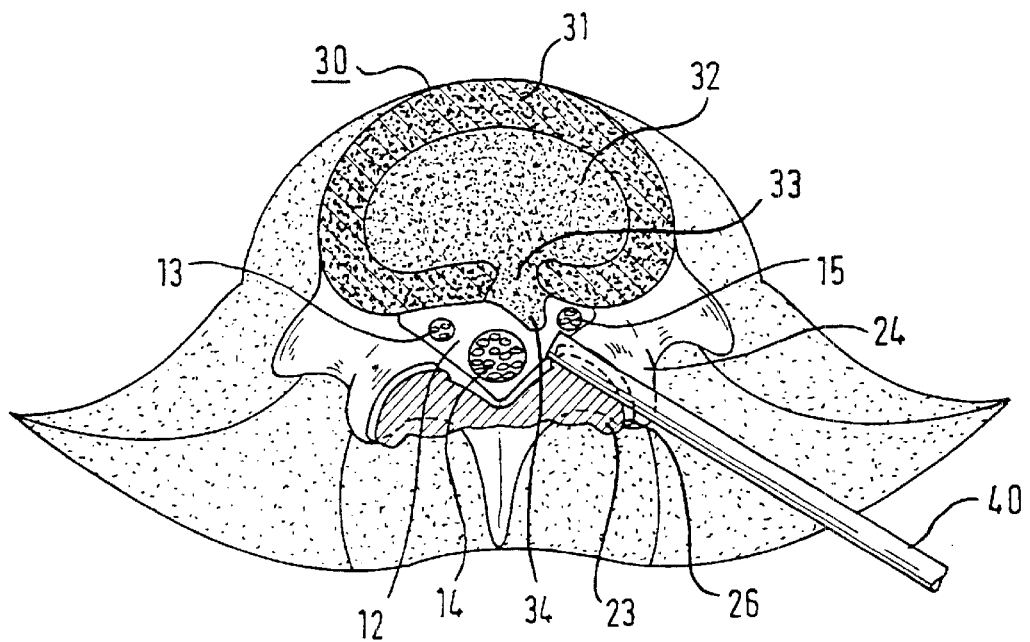
FIG. 2 is a view from above, partly in section, of the spinal disc between the two vertebrae of FIG. 1.

Reference is now made to FIG. 2 of the drawings. Here we see the disc 30 also visible in FIG. 1, with its annulus fibrosis 31 surrounding its nucleus pulposus within. There is a herniation 33 in the annulus, just to the right of the central axis of the spine, with a corresponding extrusion 34 of nucleus pulposus tissue into the vertebral canal 12. FIG. 2 clearly shows a cannula 40, introduced postero-laterally through the vertebral foramen over the facet joint 26, into the vertebral foramen 12, giving access endoscopically to the tissue bulge 34. This same cannula 40 is visible in FIG. 1. Although the distal end of cannula 40 cannot be seen in FIG. 1, FIG. 1 does show how bone material has been removed from facets 23 and 24, either side of the facet joint face 26. It is this removal of material from the facet joint, in order to gain access to the bulge of the hernia, which is key to the possibilities opened up by the present invention.

Figure 3:
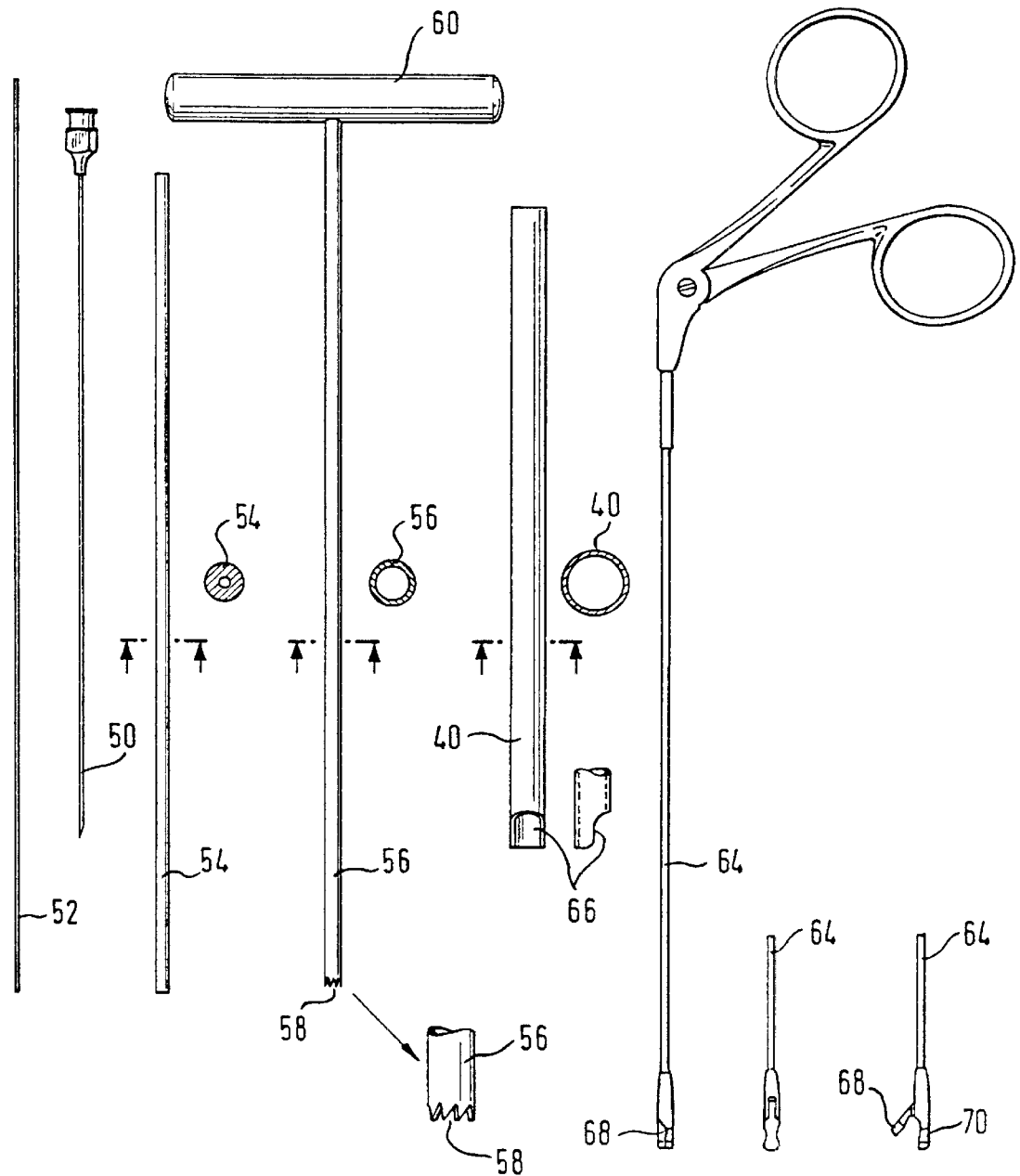
FIG. 3 shows, in longitudinal section, instruments selected from the set of instruments for performing the method of surgery described in this specification.

Referring now to FIG. 3, the method by which the cannula 40 is placed in the desired position will now be explained.

The first step is to advance a hollow needle 50, with an outside diameter of, preferably, 1.25 mm, until the distal tip of the needle is at a position adjacent the herniation. Then, a guidewire 52 is advanced through the lumen of the hollow needle, until its distal tip protrudes a short distance beyond the tip of the hollow needle 50. Next, the hollow needle 50 is withdrawn, while leaving the guidewire 52 unmoved.

Having withdrawn the hollow needle, the surgeon takes the smallest of the blunt ended trocar tubes 54 and advances that tube over the guidewire, until the blunt end of the trocar is at the facet joint 26. With the trocar in this position, the first and smallest diameter hole saw 56 is advanced over the outside surface of the trocar 54, until the distal end of the hole saw, with the cutting saw teeth 58 shown in FIG. 3, comes into abutment with the facing surfaces of the facet joint 26. At this point, the surgeon rotates manually the handle 60 at the proximal end of the hole saw 56, in order to rotate the tool and draw the teeth 58 of the hole saw across the bony material on both sides of the facet joint 26 so that, with progressive advance of the hole saw 56, a channel past the facet joint 26 is created, which has a transverse dimension, corresponding the transverse dimension of the hole saw 56.

Once this initial channel-cutting step has been performed, the hole saw 56 and the corresponding trocar tube 54 can be withdrawn, again keeping the guidewire in place without any movement. The next size of trocar is taken and advanced over the guidewire and then, in turn, the next and corresponding size of hole saw is advanced over the trocar and again rotated by the surgeon in order slightly to enlarge the transverse dimension of the channel past the facet joint 26.

Dependent of the size of the patient and the size of the herniation this same procedure is repeated twice or three times more. Once the cannula 40 is in position, it is then possible to remove from within its lumen not only the largest trocar tube but also the guidewire 52. This then leaves entirely free the lumen 62 of the cannula 40. The lumen is large enough to accommodate not only a forceps tool 64, as shown in FIG. 3, but also, if desired, an endoscope. Note that the cannula 40 is provided at its distal tip with a rebate 66 which extends around only half the circumference, to allow one jaw 68 of the forceps tool 64 to open wide while supporting the other, fixed jaw 70 of the forceps 64.

Reverting to what is shown in FIG. 2, it will be appreciated that cannula 40 with its lumen 62, gives the surgeon access to the hernia bulge 34, for its removal by the forceps tool 64, under observation of the endoscope also deployed within the lumen 62 of the cannula 40.

Should repair of the annulus 31 of the disc, adjacent the herniation 33, be deemed appropriate, following removal of the hernia material from within the vertebral foramen 12, suitable tools can be advanced through the lumen 62 of the cannula 40, again if desired under endoscopic observation.

The channel cut through the facet joint 26 is, generally speaking, harmless to the patient. The postero-lateral access to the herniation, in the vertebral foramen, as described above, has the advantage that it neither penetrates the undamaged disc annulus remote from the herniation, nor scars the nerve structures within the spine. Because the procedure is endoscopic and minimally invasive, recovery time of patients is extremely fast, rendering it possible for them to ambulate and travel home unsupervised within a very short time following the operation. Because the surgeon has the herniation under direct observation, and directly removes it from the vertebral foramen or vertebral canal, relief for the patient from the symptoms of herniation is immediate. The herniated disc furthermore has all best chances for a good recovery, reducing the likelihood of re-occurrence of herniation.

INDUSTRIAL APPLICABILITY

Millions of human beings suffer great pain from herniated lumbar vertebrae, and surgery is indicated for very large numbers of these unfortunate people. In this sense, the treatment of back pain is an extremely important "industry". In any event, there are thousands of orthopaedic surgeons and neuro surgeons around the world interested in better apparatus and methods for treating herniated discs. The subject matter of the present specification is characterised by very significant technical features, and is highly useful.

What is claimed is:

1. Apparatus for treating a herniated disc, the apparatus comprising an endoscopic soft tissue removal tool (64) and a working cannula (40) through which said tool can be advanced, the apparatus being characterised by:

a tool set (54, 56) for removing bone from a co-operating pair of superior and inferior articulating processes of the spine, to create a path for postero-lateral endoscopic access to the vertebral foramen and vertebral canal; and wherein the bone removal tool set comprises a set of trocar rods (54) of progressively increasing outside diameter, and a corresponding set of hole saw tools (56), each of which fits snugly over the outside diameter of its corresponding trocar tube and is rotatable on the tube in order to bore through the bony material around the facet joint of the spine corresponding to the herniated spinal disc under treatment.

2. Apparatus as claimed in claim 1, wherein the inside diameters of the respective hole saw tools differ by a step of 1.0 mm.

3. Apparatus as claimed in claim 1, wherein the outside diameter of the hole saw tool of largest diameter is 1.0 mm.

4. Apparatus as claimed in claim 1, including a working cannula (40) with an outside diameter corresponding to that of the outside diameter of the largest hole saw.

5. Apparatus as claimed in claim 4, wherein the distal end of the working cannula is provided with a rebate (66) which extends around only half of the circumference of the working cannula, thereby to permit one jaw of a forceps tool to be introduced within the working cannula to open wide, while the non-rebated portion of the distal tip of the working cannula supports the other jaw of the forceps tool.

* * * * *